United States Patent [19]

Saville

[11] Patent Number: Plant 7,418

[45] Date of Patent: Jan. 15, 1991

[54] MINIATURE ROSE PLANT NAMED SAVARITA

[75] Inventor: F. Harmon Saville, Rowley, Mass.

[73] Assignee: Nor'East Miniature Roses, Inc., Rowley, Mass.

[21] Appl. No.: 410,309

[22] Filed: Sep. 20, 1989

[51] Int. Cl.[5] ..... A014 5/00

[52] U.S. Cl. ..... Plt./9

[58] Field of Search ..... Plt. 9

*Primary Examiner*—Howard J. Locker

*Attorney, Agent, or Firm*—Christie, Parker & Hale

[57] ABSTRACT

A new and unusual bright pink miniature rose of old garden rose form.

1 Drawing Sheet

SUMMARY OF THE INVENTION

The present invention relates to a new and distinct variety of rose plant of the miniature rose class, which was originated by my crossing as seed parent the variety known as "Rita" and as pollen parent the variety known as "Rise 'N Shine" (U.S. Plant Pat. No. 4,231). The varietal denomination of this new rose is "Savarita."

Among the novel characteristics possessed by this new variety which distinguishes it from its parents and all other varieties of which I am aware are its bright pink flowers and unusual old garden rose form in this class of rose. Flowers open well and retain color as blooms age with only some lightening. Asexual reproduction by propagation by cuttings of the new variety as performed in Essex County, Mass., shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "55B" is plate 55B of The Royal Horticultural Society Colour Chart.

Parentage: Seedling.

*Seed parent.*—"Rita".

*Pollen parent.*—"Rise 'N Shine".

Class: Miniature.

The following observations are made of specimens grown outdoors in Essex County, Mass., during the month of July.

FLOWER

Blooming habit: Continuous.

A. Bud:

(1) *Size.*—Small.

(2) *Form.*—Ovate.

(3) *Color.*—As sepals divide, bud color is near 55B.

(4) *Sepals.*—Slightly foliated, longer than bud.

(5) *Peduncle.*—Length — about ½ inch. Aspect — straight. Strength — erect. Color — medium green.

B. Bloom:

(1) *Size.*—Average size when fully expanded — about 1¼ inch.

(2) *Borne.*—Usually in sprays of 3 to 15 blooms.

(3) *Form.*—Deeply cupped, opens to old garden rose form with quartered centers and becomes flat to convex.

(4) *Petalage.*—Number of petals under normal conditions — about 35–40.

(5) *Color.*—After sepals fall and petals unfurl, predominant flower color viewing flower top surface is deeper hued pink near 55B where petals bunch but as flowers open coloring lightens to 55C to 55D. Petal undersurface remains somewhat deeper toned, near 55B to C. General tonality at a distance is attractive bright pink. Color of petals at point of attachment is near 8D. As flowers age, coloring lightens and softens.

C. Petals:

(1) *Texture.*—Medium.

(2) *Appearance.*—Inside velvety and outside satiny.

(3) *Form.*—Nearly oval fan shape with short points at apices.

(4) *Arrangement.*—Regularly arranged, shingle-like imbricated.

(5) *Petals in center.*—Many.

(6) *Persistence.*—Drop off, but late.

(7) *Fragrance.*—None.

(8) *Lasting quality.*—Very long lasting on plant.

REPRODUCTIVE ORGANS

A. Stamens, filaments and anthers:

*Arrangement and color.*—Regularly arranged around styles, few. Color — filaments near 163C.

B. Pollen: Virtually none.
C. Styles: Medium length, thin.
D. Stigmas:
*Color.*—Near 160D.
E. Hips: None observed.

PLANT

A. Form: Spreading.
B. Growth: Very vigorous.
*Height attained.*—About 18 inches spreading also to about 18 inches.
C. Foliage: Compound 5 to 7 leaflets.
(1) *Size.*—Medium.
(2) *Quantity.*—Abundant.
(3) *Color.*—New foliage: Upper side — near 144A. Under side — near 146D. Old foliage: Upper side — near 137B. Under side — near 138B.
(4) *Shape.*—Long, oval.
(5) *Texture.*—Upper side is glossy; under side is matte.
(6) *Edge.*—Serrate.
(7) *Serration.*—Ordinary.
(8) *Leaf stem.*—Color — near 138A. Under side — 143C.

(9) *Stipules.*—Medium length, slightly bearded.
(10) *Resistance to disease.*—Blackspot — average. Mildew — average. Rust — average.
D. Wood:
(1) *New wood.*—Color — near 139C. Bark — smooth.
(2) *Old wood.*—Color — near 146B. Bark — smooth.
E. Thorns:
(1) *Thorns.*—Quantity (main stalk) — Ordinary. On laterals from stalk — few. Form — Short, thin, straight. Length — short. Color — near 186C. Position — irregular.
(2) *Prickles.*—Few, none on laterals.
F. Winter hardiness: Needs protection in severe climates.

I claim:

1. A new and distinct variety of rose plant of the miniature rose class, substantially as shown and described, characterized particularly by attractive bright pink flowers opening to old garden rose form.

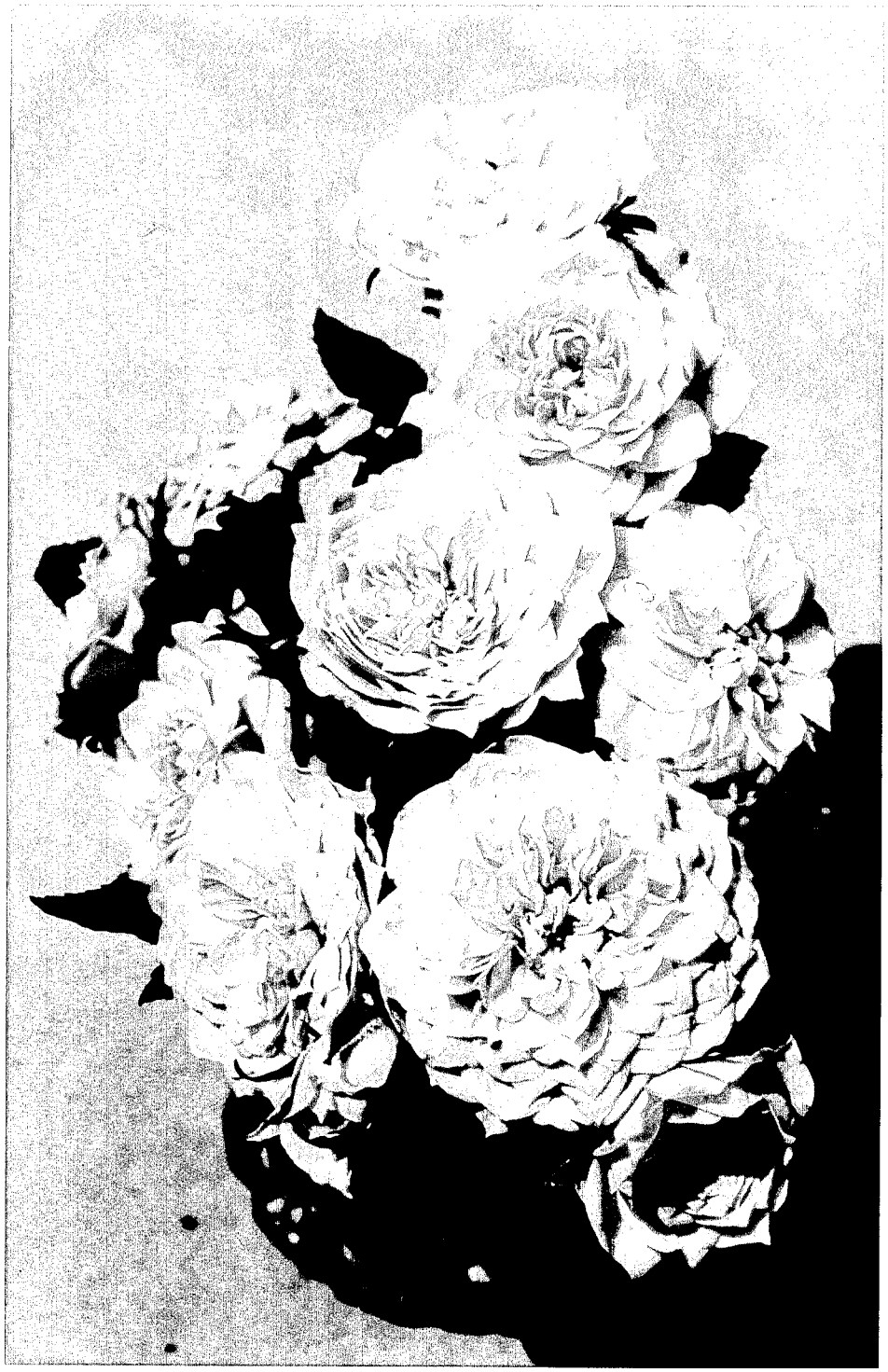

* * * * *